United States Patent
Cates et al.

(10) Patent No.: US 7,529,592 B2
(45) Date of Patent: May 5, 2009

(54) SUBCUTANEOUS ELECTRODE AND LEAD WITH TEMPORARY PHARMACOLOGICAL AGENTS

(75) Inventors: Adam W. Cates, Minneapolis, MN (US); Darrell Orvin Wagner, Isanti, MN (US); Curtis Charles Lindstrom, Roseville, MN (US); Ron Heil, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 370 days.

(21) Appl. No.: 10/703,410

(22) Filed: Nov. 7, 2003

(65) Prior Publication Data

US 2004/0230273 A1 Nov. 18, 2004

Related U.S. Application Data

(60) Provisional application No. 60/462,272, filed on Apr. 11, 2003.

(51) Int. Cl.
*A61N 1/08* (2006.01)
(52) U.S. Cl. ............... 607/120
(58) Field of Classification Search .......... 607/116, 607/119, 120
See application file for complete search history.

(56) References Cited

U.S. PATENT DOCUMENTS

| | | | |
|---|---|---|---|
| 4,146,029 A | 3/1979 | Ellinwood | |
| 4,506,680 A | 3/1985 | Stokes | |
| 4,562,841 A | 1/1986 | Brockway et al. | |
| 4,819,661 A | 4/1989 | Heil, Jr. et al. | |
| 4,819,662 A | 4/1989 | Heil, Jr. et al. | |
| 4,953,551 A | 9/1990 | Mehra et al. | |
| 5,020,544 A | 6/1991 | Dahl et al. | |
| 5,036,849 A | 8/1991 | Hauck et al. | |
| 5,041,107 A | 8/1991 | Heil, Jr. | |
| 5,090,422 A | 2/1992 | Dahl et al. | |
| 5,133,353 A | 7/1992 | Hauser | |
| 5,170,784 A | 12/1992 | Ramon et al. | |
| 5,179,945 A | 1/1993 | Van Hofwegen et al. | |
| 5,203,348 A | 4/1993 | Dahl et al. | |
| 5,209,229 A | 5/1993 | Gilli | |
| 5,230,337 A | 7/1993 | Dahl et al. | |
| 5,261,400 A | 11/1993 | Bardy | |
| 5,282,785 A | 2/1994 | Shapland et al. | |
| 5,284,136 A | 2/1994 | Hauck et al. | |
| 5,292,338 A | 3/1994 | Bardy | |
| 5,300,106 A | 4/1994 | Dahl et al. | |

(Continued)

OTHER PUBLICATIONS

"Anabolic steroid", wikipedia.com.*

(Continued)

*Primary Examiner*—Carl H Layno
*Assistant Examiner*—Eric D Bertram
(74) *Attorney, Agent, or Firm*—Hollingsworth & Funk, LLC

(57) ABSTRACT

An implantable subcutaneous device and method employ a lead and an electrode for cardiac monitoring and intervention. The device includes an implantable lead having a lead body, a subcutaneous electrode coupled to the lead body, and a pharmacological agent provided on the implantable lead and/or electrode. The pharmacological agent provides a temporary therapeutic treatment to subcutaneous non-intrathoracic tissue. A method of implanting subcutaneous leads involves providing a lead including a lead body, a subcutaneous electrode, and a pharmacological agent, and delivering the pharmacological agent to subcutaneous non-intrathoracic tissue surrounding the lead.

111 Claims, 9 Drawing Sheets

U.S. PATENT DOCUMENTS

| | | | |
|---|---|---|---|
| 5,301,677 A | 4/1994 | Hsung | |
| 5,313,953 A | 5/1994 | Yomtov et al. | |
| 5,314,430 A | 5/1994 | Bardy | |
| 5,314,459 A | 5/1994 | Swanson et al. | |
| 5,324,324 A * | 6/1994 | Vachon et al. | 607/120 |
| 5,331,966 A | 7/1994 | Bennett et al. | |
| 5,360,442 A | 11/1994 | Dahl et al. | |
| 5,366,496 A | 11/1994 | Dahl et al. | |
| 5,372,606 A | 12/1994 | Lang et al. | |
| 5,376,106 A | 12/1994 | Stahmann et al. | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,405,362 A | 4/1995 | Kramer et al. | |
| 5,411,031 A | 5/1995 | Yomtov | |
| 5,411,525 A | 5/1995 | Swanson et al. | |
| 5,411,539 A | 5/1995 | Neisz | |
| 5,439,482 A | 8/1995 | Adams et al. | |
| 5,441,518 A | 8/1995 | Adams et al. | |
| 5,468,254 A | 11/1995 | Hahn et al. | |
| 5,531,779 A | 7/1996 | Dahl et al. | |
| 5,545,202 A | 8/1996 | Dahl et al. | |
| 5,603,732 A | 2/1997 | Dahl et al. | |
| 5,620,466 A | 4/1997 | Haefner et al. | |
| 5,628,730 A | 5/1997 | Shapland et al. | |
| 5,634,938 A | 6/1997 | Swanson et al. | |
| 5,641,326 A | 6/1997 | Adams | |
| 5,662,688 A | 9/1997 | Haefner et al. | |
| 5,683,447 A * | 11/1997 | Bush et al. | 607/126 |
| 5,697,953 A | 12/1997 | Kroll et al. | |
| 5,704,365 A | 1/1998 | Albrecht et al. | |
| 5,724,984 A | 3/1998 | Arnold et al. | |
| 5,749,909 A | 5/1998 | Schroeppel et al. | |
| 5,788,979 A * | 8/1998 | Alt et al. | 424/426 |
| 5,807,306 A | 9/1998 | Shapland et al. | |
| 5,827,326 A | 10/1998 | Kroll et al. | |
| 5,895,414 A | 4/1999 | Sanchez-Zambrano | |
| 5,916,243 A | 6/1999 | KenKnight et al. | |
| 5,957,956 A | 9/1999 | Kroll et al. | |
| 5,987,746 A | 11/1999 | Williams | |
| 6,044,298 A | 3/2000 | Salo et al. | |
| 6,055,454 A | 4/2000 | Heemels | |
| 6,099,567 A | 8/2000 | Badylak et al. | |
| 6,134,470 A | 10/2000 | Hartlaub | |
| 6,144,879 A | 11/2000 | Gray | |
| 6,148,230 A | 11/2000 | KenKnight | |
| 6,167,305 A | 12/2000 | Cammilli | |
| 6,168,801 B1 | 1/2001 | Heil, Jr. et al. | |
| 6,178,349 B1 | 1/2001 | Kieval | |
| 6,280,462 B1 | 8/2001 | Hauser et al. | |
| 6,282,444 B1 | 8/2001 | Kroll et al. | |
| 6,295,474 B1 * | 9/2001 | Munshi | 607/121 |
| 6,304,786 B1 * | 10/2001 | Heil et al. | 607/126 |
| 6,360,129 B1 | 3/2002 | Ley et al. | |
| 6,361,780 B1 * | 3/2002 | Ley et al. | 424/400 |
| 6,409,675 B1 | 6/2002 | Turcott | |
| 6,415,174 B1 | 7/2002 | Bebehani et al. | |
| 6,416,510 B1 | 7/2002 | Altman et al. | |
| 6,436,068 B1 | 8/2002 | Bardy | |
| 6,438,410 B2 | 8/2002 | Hsu et al. | |
| 6,475,232 B1 | 11/2002 | Babbs et al. | |
| 6,478,776 B1 | 11/2002 | Rosenman et al. | |
| 6,480,733 B1 | 11/2002 | Turcott | |
| 6,491,639 B1 | 12/2002 | Turcott | |
| 6,512,940 B1 | 1/2003 | Brabec et al. | |
| 6,522,915 B1 | 2/2003 | Ceballos et al. | |
| 6,564,106 B2 | 5/2003 | Guck et al. | |
| 6,584,363 B2 | 6/2003 | Heil, Jr. et al. | |
| 6,607,509 B2 | 8/2003 | Bobroff et al. | |
| 6,615,083 B2 | 9/2003 | Kupper | |
| 6,622,046 B2 | 9/2003 | Fraley et al. | |
| 7,190,997 B1 | 3/2007 | Parvish et al. | |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035380 A1 | 3/2002 | Rissmann et al. | |
| 2002/0035381 A1 | 3/2002 | Bardy et al. | |
| 2002/0042629 A1 | 4/2002 | Bardy et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0049476 A1 | 4/2002 | Bardy et al. | |
| 2002/0052636 A1 | 5/2002 | Bardy et al. | |
| 2002/0068958 A1 | 6/2002 | Bardy et al. | |
| 2002/0072773 A1 | 6/2002 | Bardy et al. | |
| 2002/0082658 A1 | 6/2002 | Heinrich et al. | |
| 2002/0091414 A1 | 7/2002 | Bardy et al. | |
| 2002/0095184 A1 | 7/2002 | Bardy et al. | |
| 2002/0103510 A1 | 8/2002 | Bardy et al. | |
| 2002/0107544 A1 | 8/2002 | Ostroff et al. | |
| 2002/0107545 A1 | 8/2002 | Rissmann et al. | |
| 2002/0107546 A1 | 8/2002 | Ostroff et al. | |
| 2002/0107547 A1 | 8/2002 | Erlinger et al. | |
| 2002/0107548 A1 | 8/2002 | Bardy et al. | |
| 2002/0107549 A1 | 8/2002 | Bardy et al. | |
| 2002/0107559 A1 | 8/2002 | Sanders et al. | |
| 2002/0120299 A1 | 8/2002 | Ostroff et al. | |
| 2002/0138123 A1 | 9/2002 | Casas-Bejar et al. | |
| 2003/0004546 A1 | 1/2003 | Casey | |
| 2003/0004552 A1 | 1/2003 | Plombon et al. | |
| 2003/0023175 A1 | 1/2003 | Arzbaecher et al. | |
| 2003/0036778 A1 | 2/2003 | Ostroff et al. | |
| 2003/0045904 A1 | 3/2003 | Bardy et al. | |
| 2003/0069609 A1 | 4/2003 | Thompson | |
| 2003/0088278 A1 | 5/2003 | Bardy et al. | |
| 2003/0088279 A1 | 5/2003 | Rissmann et al. | |
| 2003/0088280 A1 | 5/2003 | Ostroff | |
| 2003/0088281 A1 | 5/2003 | Ostroff et al. | |
| 2003/0088282 A1 | 5/2003 | Ostroff | |
| 2003/0088283 A1 | 5/2003 | Ostroff | |
| 2003/0088286 A1 | 5/2003 | Ostroff et al. | |
| 2003/0097153 A1 | 5/2003 | Bardy et al. | |
| 2003/0212436 A1 | 11/2003 | Brown | |

OTHER PUBLICATIONS

Smith et al., "Analysis of Chromameter Results Obtained from Corticosteroid-Induced SKin Blanching". Pharmaceutical Research, col. 15, No. 2, Abstract (1998).*

Gilron et al. "Preemptive analgesic effects of steroid anesthesia with alphaxalone in the rat formalin test." Anesthesiology, Mar. 1996; 84(3): Abstract.*

Demling et al. "The rate of restoration of body weight after burn injury, using the anabolic agent oxandrolone, is not age dependent." Burns (Feb. 2001). 27 (1). Abstract.*

Renee Hartz et al., *New Approach to Defibrillator Insertion*, J. Thoracic Cardiovascular Surgery, vol. 97, pp. 920-922 (1989).

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at col. 778, p. B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

"Anabolic Steroid", wikipedia.org.

Smith et al., "Analysis of Chromameter Results Obtained from Corticosteroid-Induced Skin Blanching", Pharmaceutical Research, col. 15, No. 2, Abstract Only (1998).

Gilron et al., "Preemptive Analgesic Effects of Steroid Anesthesia with Alphaxalone in the Rat Formalin Test", Anesthesiology, Mar. 1996, 84(3), Abstract Only.

Demling et al., "The Rate of Restoration of Body Weight after Burn Injury, Using the Anabolic Agent Oxandrolone, is Not Age Depentdent", Burns, Feb. 2001, 27(1), Abstract Only.

Smits et al., *Defibrillation Threshold (DFT) Model of a Fully Subcutaneous ICD System*, Europace Supplements, vol. 2, Jun. 2001 at col. 778, p. B83.

\* cited by examiner

SUBCUTANEOUS ELECTRODE AND LEAD WITH TEMPORARY PHARMACOLOGICAL AGENTS

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to leads for subcutaneously implantable cardioverters/defibrillators and monitors, and, more particularly, to subcutaneously implantable leads provided with pharmacological agents.

BACKGROUND OF THE INVENTION

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators (ICDs) include one or more endocardial leads to which at least one defibrillation electrode is connected. Such ICDs are capable of delivering high-energy shocks to the heart, interrupting the ventricular tachyarrythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. The primary reasons for this unfortunate reality include the limited number of physicians qualified to perform transvenous lead/electrode implantation, a limited number of surgical facilities adequately equipped to accommodate such cardiac procedures, and a limited number of the at-risk patient population that can safely undergo the required endocardial or epicardial lead/electrode implant procedure. For this reason, subcutaneous ICDs are being developed to overcome these issues.

For reasons stated above, and for other reasons which will become apparent to those skilled in the art upon reading the present specification, there is a need for systems and methods that provide for sensing cardiac activity and delivering defibrillation and/or pacing therapies without the need for endocardial or epicardial leads/electrodes. There is a particular need for subcutaneous leads that improve patient comfort, reduce morbidity, and improve surgical outcomes. The present invention fulfills these and other needs, and addresses deficiencies in known systems and techniques.

SUMMARY OF THE INVENTION

The present invention is directed to subcutaneous leads and methods of using subcutaneous leads that improve patient comfort, reduce morbidity, and improve surgical outcomes by incorporating pharmacological agents. The device has an implantable lead including a lead body, a subcutaneous electrode coupled to the lead body and a pharmacological agent provided on the lead and/or electrode. The pharmacological agent provides a temporary therapeutic treatment to subcutaneous non-intrathoracic tissue. An implantable cardioverter/defibrillator system is also disclosed including a can with an implantable lead. One or more pharmacological agents may be provided on the lead and/or electrode and/or can.

An embodiment of the present invention concerns combinations of pharmacological agents on leads, electrodes, and/or device housings (e.g., cans, active or non-active). Pharmacological agents with short temporary activity provided on electrodes are also described in combination with pharmacological agents on the can and/or lead body that can have longer term activity so as not to adversely interfere with electrical properties of the implantable cardioverter/defibrillator system.

A method of implanting subcutaneous leads is described including providing a lead having a lead body, a subcutaneous electrode, and a pharmacological agent and delivering the pharmacological agent to subcutaneous non-intrathoracic tissue. The method may include providing a sheath and inserting the lead into the sheath.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
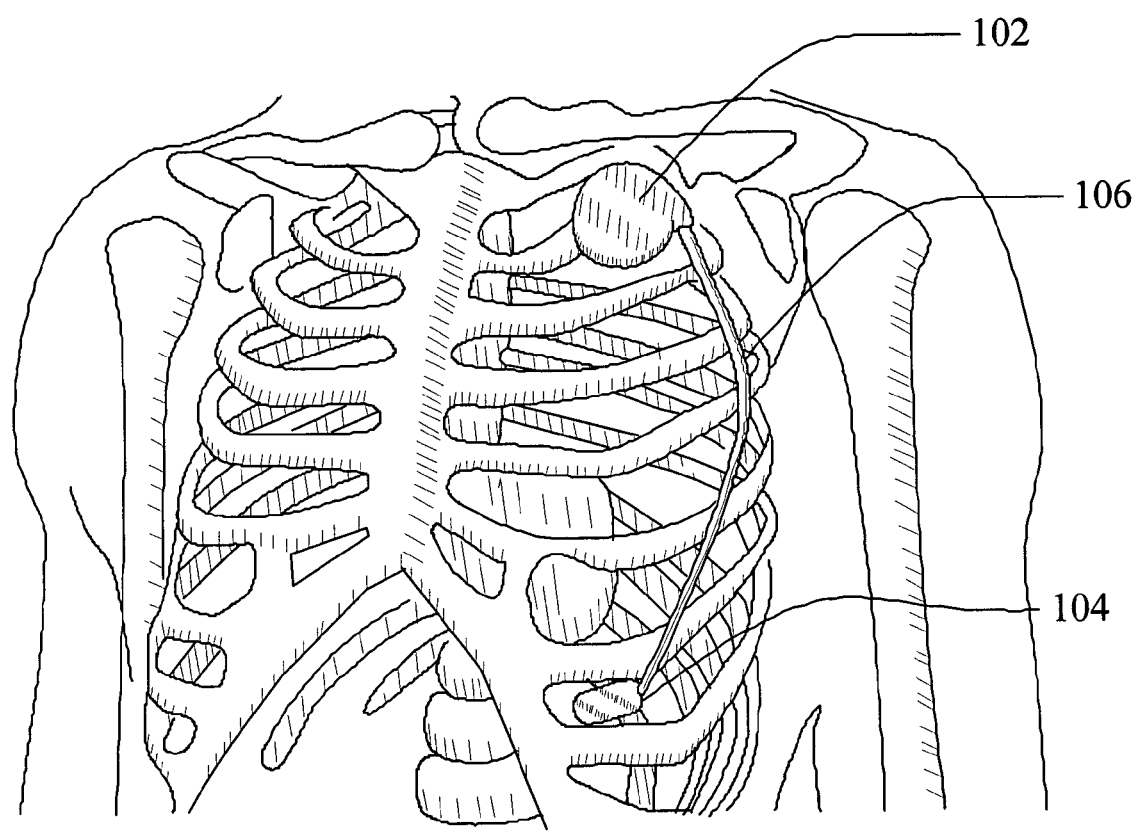
FIGS. 1A and 1B are views of a transthoracic cardiac monitoring and/or stimulation device as implanted in a patient.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

A device employing an implantable lead implemented in accordance with the present invention can incorporate one or more of the features, structures, methods, or combinations thereof described herein below. For example, a subcutaneous cardiac monitor or stimulator can be implemented to include one or more of the advantageous features and/or processes described below. It is intended that such a device or method need not include all of the features and functions described herein, but can be implemented to include selected features and functions that provide for unique structures and/or functionality.

In general terms, an implantable lead implemented in accordance with the present invention can be used with a subcutaneous cardiac monitoring and/or stimulation device. One such device is an implantable transthoracic cardiac sensing and/or stimulation (ITCS) device that can be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, can be configured for positioning outside of the rib cage at an intercostal or subcostal location, within the abdomen, or in the upper chest region (e.g., subclavian location, such as above the third rib). In one implementation, one or more electrodes can be located on the primary housing and/or at other locations about, but not in direct contact with the heart, great vessel or coronary vasculature.

In another implementation, one or more leads incorporating electrodes can be located in direct contact with the heart, great vessel or coronary vasculature, such as via one or more leads implanted by use of conventional transvenous delivery approaches. In another implementation, for example, one or more subcutaneous electrode subsystems or electrode arrays can be used to sense cardiac activity and deliver cardiac stimulation energy in an ITCS device configuration employing an active can or a configuration employing a non-active can. Electrodes can be situated at anterior and/or posterior locations relative to the heart.

Figure 1B:
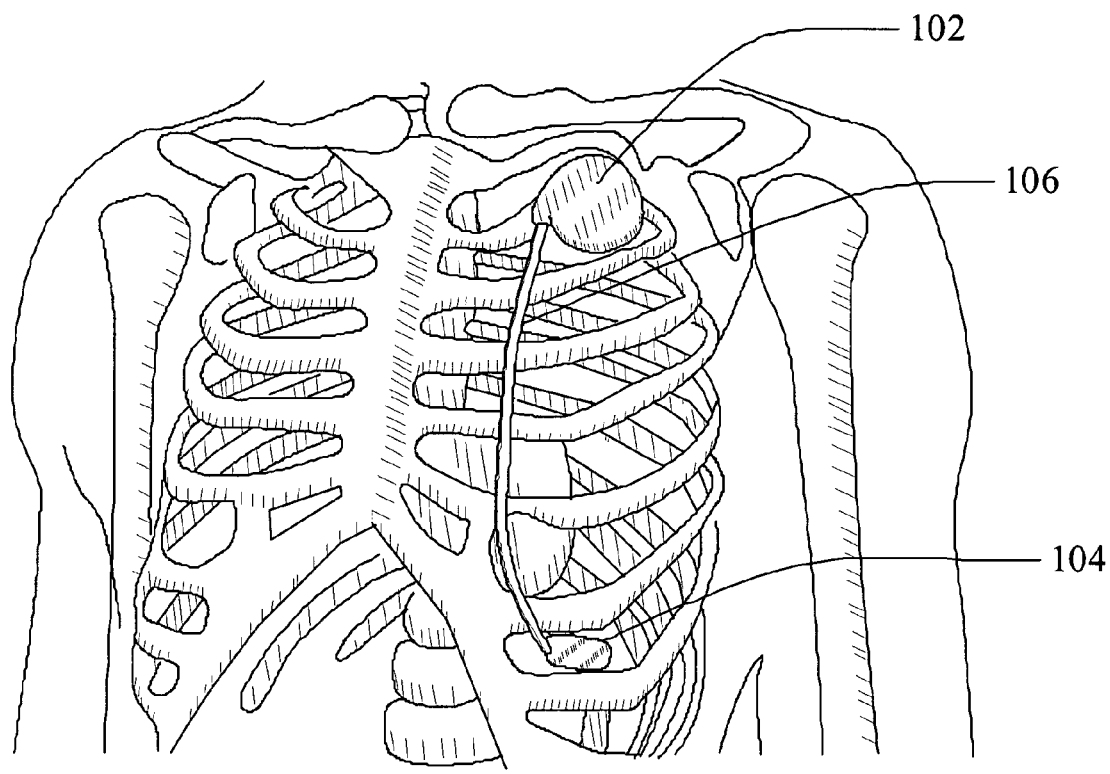

Referring now to FIGS. 1A and 1B of the drawings, there is shown a configuration of a transthoracic cardiac sensing and/or stimulation (ITCS) device having components implanted in the chest region of a patient at different locations by use of a dissection tool. In the particular configuration shown in FIGS. 1A and 1B, the ITCS device includes a housing 102 within which various cardiac sensing, detection, processing, and energy delivery circuitry can be housed. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed. An ITCS system according to this approach is distinct from conventional approaches in that it is preferably configured to include a combination of two or more electrode subsystems that are implanted subcutaneously.

In the configuration shown in FIGS. 1A and 1B, a subcutaneous electrode 104 can be positioned under the skin in the chest region and situated distal from the housing 102. The subcutaneous and, if applicable, housing electrode(s) can be positioned about the heart at various locations and orientations, such as at various anterior and/or posterior locations relative to the heart. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes can be situated on the elongated structure of the electrode support or the lead body 106, the housing 102, and/or the distal electrode assembly (shown as subcutaneous electrode 104 in the configuration shown in FIGS. 1A and 1B).

In one configuration, the lead assembly 106 is generally flexible. In another configuration, the lead assembly 106 is constructed to be somewhat flexible, yet has an elastic, spring, or mechanical memory that retains a desired configuration after being shaped or manipulated by a clinician. For example, the lead assembly 106 can incorporate a gooseneck or braid system that can be distorted under manual force to take on a desired shape. In this manner, the lead assembly 106 can be shape-fit to accommodate the unique anatomical configuration of a given patient, and generally retains a customized shape after implantation. Shaping of the lead assembly 106 according to this configuration can occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure can be formed from a structural plastic, composite or metallic material, and comprises, or is covered by, a biocompatible material. Appropriate electrical isolation between the housing 102 and the subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure can have, for example, an arcuate or angled shape.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement can be configured to include both electrical and mechanical couplings that provide for mechanical and electrical connections between the rigid electrode support assembly and housing 102. The header block arrangement can be provided on the housing 102 or the rigid electrode support assembly, or both the housing 102 and the rigid electrode support assembly. Alternatively, a mechanical/electrical coupler can be used to establish mechanical and electrical connections between the rigid electrode support assembly and the housing 102. In such a configuration, a variety of different electrode support assemblies of varying shapes, sizes, and electrode configurations can be made available for physically and electrically connecting to a standard ITCS device.

It is noted that the electrodes and the lead assembly 106 can be configured to assume a variety of shapes. For example, the lead assembly 106 can have a wedge, chevron, flattened oval, or a ribbon shape, and the subcutaneous electrode 104 can comprise a number of spaced electrodes, such as an array or band of electrodes. Moreover, two or more subcutaneous electrodes 104 can be mounted to multiple electrode support assemblies 106 to achieve a desired spaced relationship amongst the subcutaneous electrodes 104. Accordingly, subcutaneous leads of the present invention can be shaped appropriately for specific electrodes or families of electrodes and electrode support assemblies.

Figure 2A:
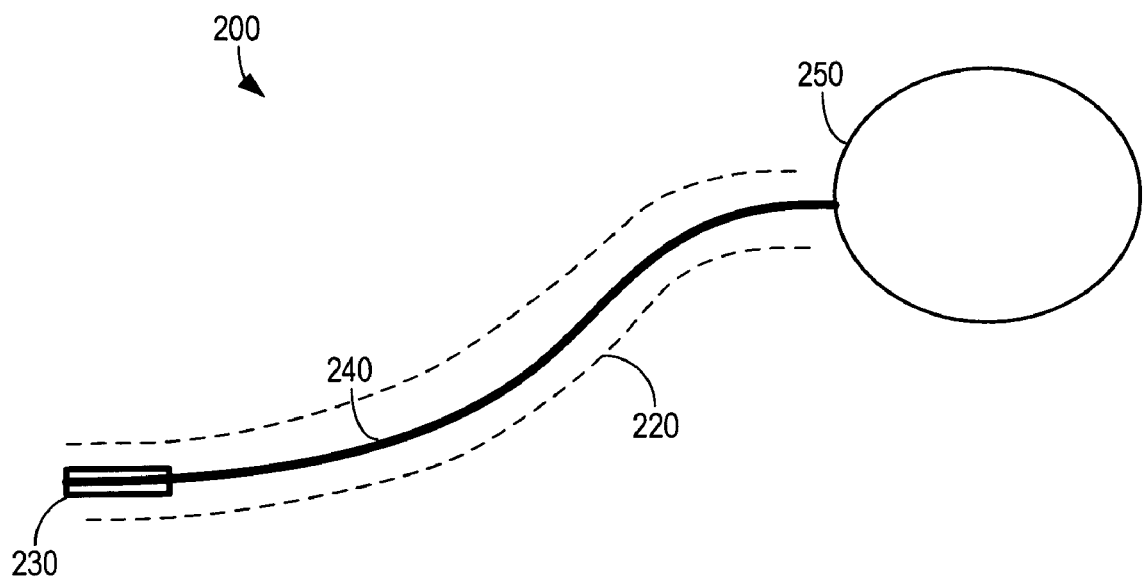
FIG. 2A illustrates a lead in accordance with the present invention, inserted in a dissected subcutaneous path leading from the can.

Referring now to FIG. 2A, an ITCS system 200 is illustrated including a can 250 with a lead 240 inserted into a dissection path 220. The lead 240 includes an electrode 230, here illustrated at the distal end of the lead 240. The dissection path 220 lies within the subcutaneous tissue of a patient as illustrated in FIGS. 1A and 1B.

Figure 2B:
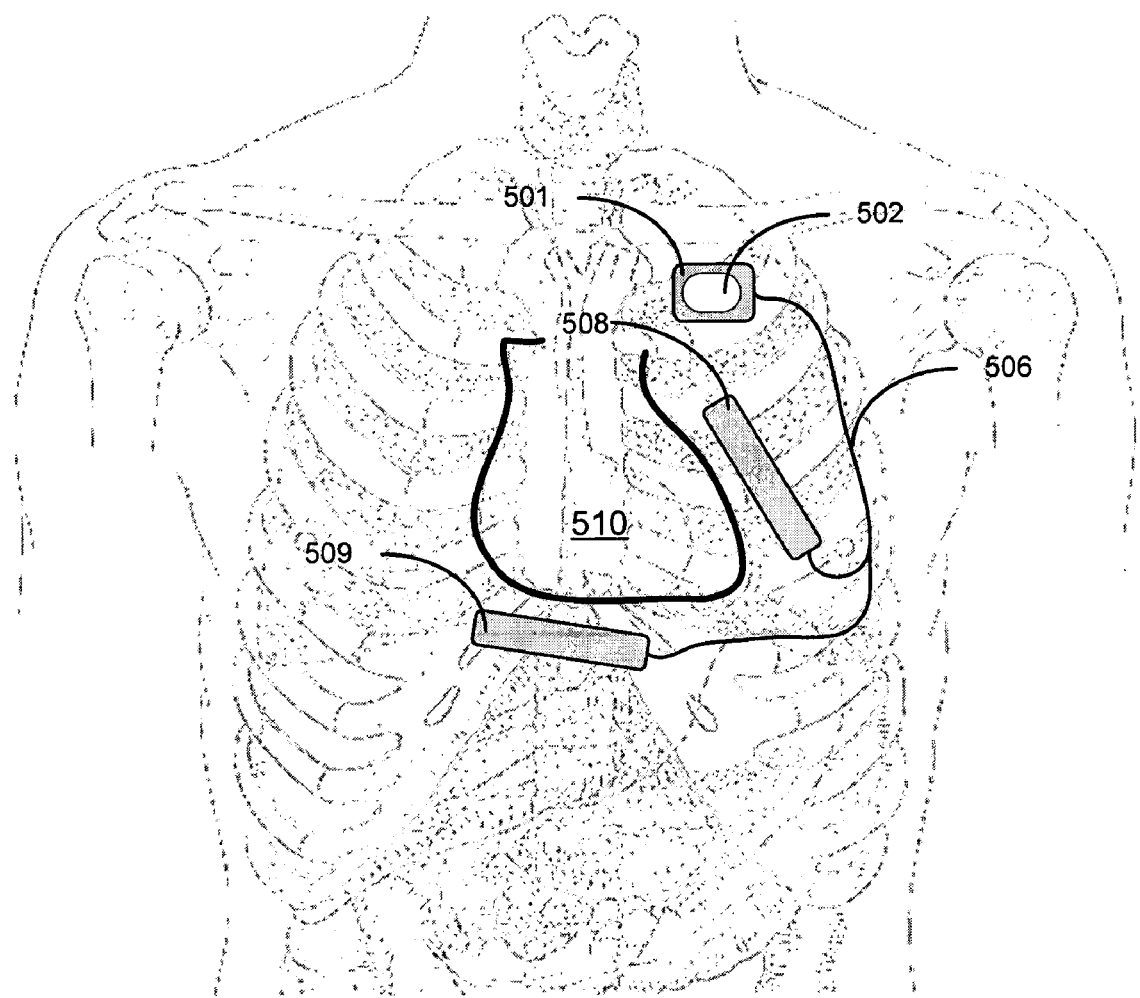
FIG. 2B illustrates various components of a transthoracic cardiac sensing and/or stimulation device positioned in accordance with embodiments of the invention.

Referring to FIG. 2B, a can electrode 502 is positioned on a housing 501 that encloses the ITCS device electronics. In one embodiment, the can electrode 502 comprises the entirety of the external surface of housing 501. In other embodiments, various portions of the housing 501 may be electrically isolated from the can electrode 502 or from tissue. For example, the active area of the can electrode 502 may comprise all or a portion of either the anterior or posterior surface of the housing 501 to direct current flow in a manner advantageous for cardiac sensing and/or stimulation.

The housing 501 may resemble that of a conventional implantable ICD, is approximately 20-100 cc in volume, with a thickness of 0.4 to 2 cm and with a surface area on each face of approximately 30 to 100 $cm^2$. As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example. These coating materials can be infused with one or more pharmacological agents as described below in greater detail.

In addition, or alternatively, all or portions of the housing 501 may be treated to change the electrical conductivity characteristics thereof for purposes of optimally directing current flow. Various known techniques can be employed to modify the surface conductivity characteristics of the housing 501, such as by increasing or decreasing surface conductivity, to optimize current flow. Such techniques can include those that mechanically or chemically alter the surface of the housing 501 to achieve desired electrical conductivity characteristics.

In the configuration shown in FIG. 2B, the ITCS device housing 501 containing the electronics (i.e., the can) is not used as an electrode. In this case, an electrode system comprising two electrode subsystems 508, 509 coupled to the housing 501 may be implanted subcutaneously in the chest region of the body, such as in the anterior thorax. The first and the second electrode subsystems 508, 509 are placed in opposition with respect to the ventricles of a heart 510, with the majority of the ventricular tissue of the heart 510 included within a volume defined between the electrode subsystems 508, 509. As illustrated in FIG. 2B, the first electrode system 508 is positioned superior to the heart 510 relative to a superior aspect of the heart 510, e.g., parallel to the left ventricular free wall. The second electrode system 509 is located inferior to the heart 510 and positioned in relation to an inferior aspect of the heart 510, e.g., parallel to the right ventricular free wall. A cable or wiring 506 conductively couples the electrode subsystems 508, 509 to the housing 501.

In this configuration, the first and the second electrode subsystems 508 and 509 may comprise any combination of electrodes used for sensing and/or electrical stimulation. In various configurations, the electrode subsystems 508, 509 may each be comprised of a single electrode or a combination of electrodes. The electrode or electrodes comprising the first and second electrode subsystems 508, 509 may include any combination of one or more coil electrodes, tip electrodes, ring electrodes, multi-element coils, spiral coils, spiral coils mounted on non-conductive backing, and screen patch electrodes, for example.

Figure 3:
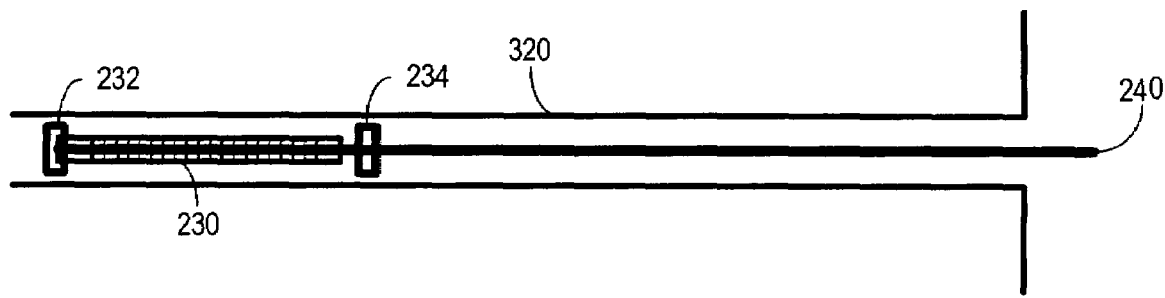
FIG. 3 is a plan view of a lead incorporating pharmacological agents in accordance with the present invention, enclosed within a sheath.

Referring to FIGS. 2A and 2B, the lead 240 and/or the electrode subsystems 508, 509 may be inserted into the dissection path 220 (FIG. 2A) by themselves, or may also be inserted with use of a sheath 320 as illustrated in FIG. 3. In FIG. 3, a proximal end of the lead 240 extends from the sheath 320, with the electrode 230 enclosed within the lumen of the sheath 320. The electrode 230 is illustrated with pharmacological agents 232 and 234 provided at distal and proximal ends of the electrode 230 respectively. It is understood that one, two, or more than two pharmacological agents can be provided at the electrode, and that provision of agents 232 and 234 is for illustrative purposes only.

The pharmacological agents 232 and 234 may be incorporated with the lead 240 via, for example, a collar, a porous region, a coating, or other suitable means. The lead 240 may be inserted into the dissection path 220 (FIG. 2A) inside the sheath 320. After properly locating the lead 240 within the subcutaneous tissue, the sheath 320 may be retracted from the subcutaneous tunnel thereby exposing the pharmacological agents 232 and 234 to the surrounding tissue and initiating a period of pharmacological activity by allowing drug(s) within pharmacological agents 232 and 234 to diffuse into the tissue surrounding the lead 240.

A non-limiting, non-exhaustive list of suitable pharmacological agents 232 and 234 includes analgesics, anesthetics, antibiotics, antiseptics, steroids, anti-inflammatory drugs, agents that promote hemostasis, agents that provide vasoconstriction, collagen, and agents that increase the rate of healing. Suitable analgesics or anesthetics may be, for example, aspirin, IBUPFOFEN, BUPIVACAINE, LIDOCAINE, MAPRIVACAINE and PROCAINE. Suitable steroids may be, for example, DEXAMETHASONE and BETAMETHASONE. A suitable pharmacological agent that provides vasoconstriction may be, for example, EPINEPHRINE. Suitable antibiotics or antiseptics may be, for example, VANCOMYCIN and CEFALOZIN. A suitable pharmacological agent that can increase the rate of healing may be, for example, stomach submucosa derived tissue such as disclosed in U.S. Pat. No. 6,099,567, which is hereby incorporated herein by reference.

Figure 4:
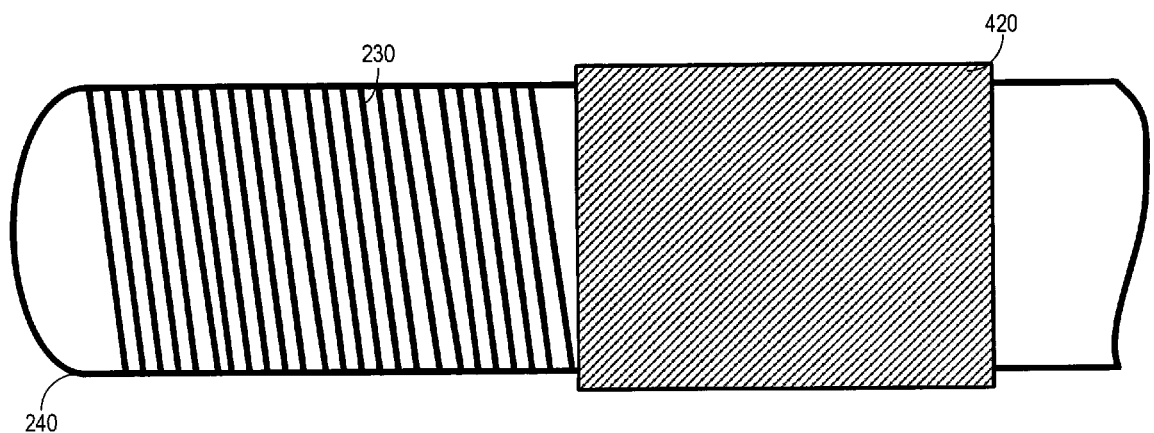
FIG. 4 is a magnified view of a lead with an electrode incorporating pharmacological agents in accordance with the present invention.

FIG. 4 illustrates an embodiment of the lead 240 with an electrode 230 and a coating 420. The coating 420 contains a pharmacological agent that is desired near the distal end of the lead 240. The coating 420 may be placed on the lead 240 by, for example, painting, spraying, dipping, vapor deposition, or other suitable means.

The lead 240 may be masked before applying the coating 420. For example, it may be desirable to place the coating 420 close to the electrode 230, as illustrated in FIG. 4, without covering the electrode 230. This may be accomplished by masking the electrode 230, spraying or dipping the coating 420, and then removing the masking, leaving the coating 420 in place without covering the electrode 230. It may be desirable to mask the electrode 230 if, for example, the pharmacological agent has an activity lasting more than one day. However, provision of the coating 420 covering the electrode 230 may alter the operating characteristics of the electrode 230.

Figure 5:
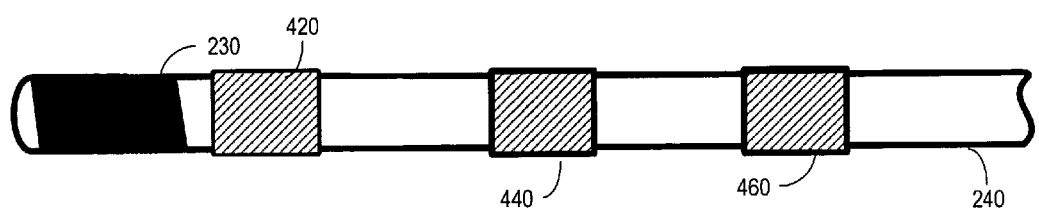
FIG. 5 is a magnified view of another embodiment of a lead with an electrode incorporating pharmacological agents in accordance with the present invention.

Referring now to FIG. 5, another embodiment of the lead 240 is illustrated, now with a second application 440 and a third application 460 of pharmacological agents in addition to the coating 420. It may be useful, for example, to periodically provide pharmacological agents along a portion of the length of the lead 240 to provide analgesia. Pharmacological agents may be applied at discrete locations, as illustrated in FIG. 5, or may be continuous along all or part of the lead 240. For example, an analgesic may be applied along a major portion (e.g. more than 25%) of lead 240, except on the electrode 230 where it may hinder electrical performance.

It may also be useful to apply a coating along a portion of the entire length of the lead 240 with, for example, an antiseptic, and also provide the coating 420 and/or second application 440 and/or third application 460 with, for example, an analgesic. This combination provides analgesia that diffuses locally to the dissected tissue surrounding the lead 240, while simultaneously providing an inhibition of infection along the dissection path. A temporary combination such as this may provide improved patient comfort and acceptance of the implant with improved outcomes and less morbidity from the procedure.

Pharmacological agents for use in accordance with the present invention provide a temporary effectiveness within the patient. The term temporary may have both quantitative and qualitative meanings. For example, direct analgesia may be desirable to tissue surrounding the dissection path immediately following the implantation procedure, to provide improved patient comfort between anesthesia during the procedure and any post-procedure medication. The quantitative time period of interest may be about one hour in this case. Qualitatively, for example, it would be beneficial to provide site-specific anesthesia or analgesia for the duration of time between when the general anesthesia wears off and when a post-operative oral analgesic has reached an effective concentration level to provide pain relief, or to provide sufficient time duration such that oral analgesia is not necessary.

Another qualitative example of the term temporary as presently contemplated includes the use of an antiseptic agent delivered during the implantation procedure, and for a time period thereafter sufficient to reduce the morbidity of sepsis. The quantitative time frame for antisepsis may be on the order of hours, whereas for antibiotics, for example, a course of treatment often lasts ten days to several weeks. Qualitatively, it may be desirable to provide an antibiotic treatment from a portion of, or all of, the implanted device from the time of implantation until the probability of morbidity is diminished. Depending on patient variability and disease state, quantitatively, antibiosis may be desirable from about three days to more than about three weeks.

Other pharmacological agents in accordance with the present invention may have different quantitative and qualitative time frames associated with their effectiveness. For example, a xenograft collagen membrane that may be used to decrease the time necessary to heal from a tissue dissection, may be implanted as a permanent graft. However, the body will use the xenograft tissue as a scaffolding to increase the healing rate, but over time remodel the graft tissue to native tissue. The determination of when xenographic tissue is converted to native tissue is too imprecise to provide a precise quantitative time-frame applicable to all patients.

Therefore, for purposes herein, the term temporary is meant to encompass both the quantitative and qualitative aspects of pharmacological agents having an effectiveness for a limited time-period, the time period varying depending on the particular pharmacological activity desired. A non-exhaustive, non-limiting list of pharmacological activities includes: antisepsis, antibiosis, analgesia, anesthesia, vasoconstriction, and hemostasis.

Figure 6:
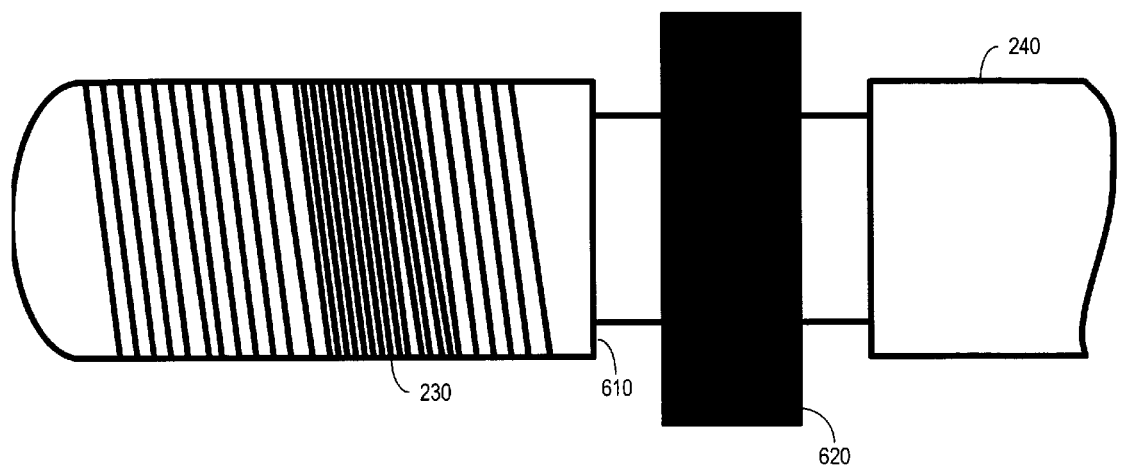
FIG. 6 is a magnified view of another embodiment of a lead with an electrode incorporating pharmacological agents in accordance with the present invention.

FIG. 6 illustrates another embodiment of the present invention. In FIG. 6, the lead 240 is shown to have a groove 610 providing a fixation point for a collar 620. Collar 620 may be, for example, a silicone collar impregnated with a pharmacological agent. Collars impregnated with pharmacological agents are known in the art such as, for example, collars described in U.S. Pat. No. 6,361,780 ('780) hereby incorporated herein by reference. Activity periods and dosage delivery of pharmacological agents can be tailored to the application by appropriate manufacture of the collar 620.

Although the width of groove 610 is illustrated in FIG. 6 to be significantly larger than the width of the collar 620, any desirable relationship may be provided. For example, the collar 620 may be provided with a plurality of layers incorporating a plurality of pharmacological agents, and/or a plurality of pharmological activities. This would provide the potential for a tiered delivery of drug activity. For example, the outer layer may provide an acute high dosage for a short duration, while subsequent layers provide a longer term delivery.

In another embodiment of the present invention, an outermost layer of the collar 620 may provide analgesia while subsequent layers provide antibiosis and healing accelerators. By varying the width of the groove 610, and fitment of the collar 620, diffusion of the pharmacological agents from the layers of the collar 620 can be controlled to provide combinations of tiered therapy.

Figure 7:
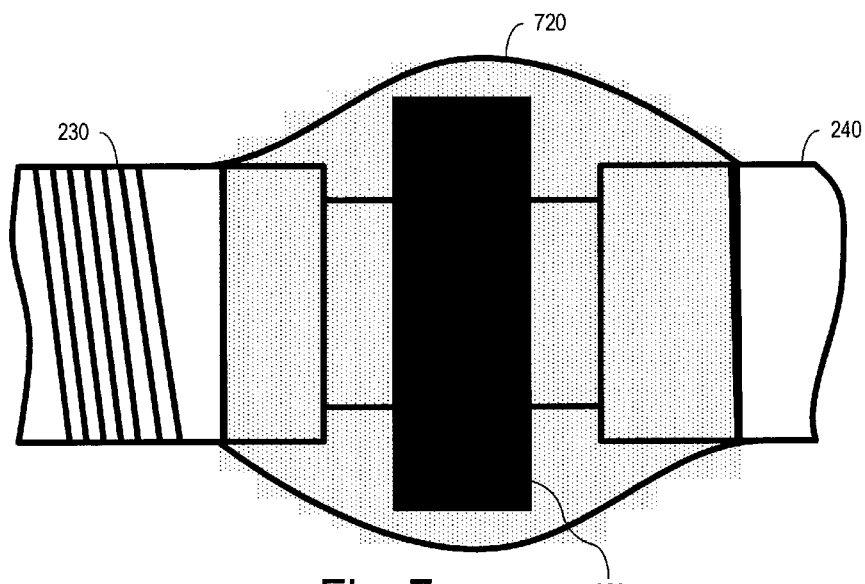
FIG. 7 is a magnified view of another embodiment of a lead with an electrode incorporating pharmacological agents in accordance with the present invention.

Yet another embodiment of the present invention is illustrated in FIG. 7. An encapsulation 720 encloses the collar 620 within the encapsulation 720. The encapsulation 720 may include a first pharmacological treatment wherein the encapsulation 720 dissolves away from the lead 240 over time. After a period of time, the encapsulation 720 is removed from the collar 620, exposing the collar 620 and providing a second pharmacological treatment. The first and second pharmacological treatments may vary by, for example, dosage intensities, pharmacological activities, therapy type, or other desired treatment. For example, the encapsulation 720 may be a non-dissolving semi-permeable membrane with the intent being the regulation of the diffusion rate from the collar 620 while protecting the collar 620 from the host body foreign object response.

In yet another embodiment, the lead 240 body material itself may be used to deliver a pharmacological agent. The normal lead 240 insulation may be used as the drug carrier. In practice, the polymeric insulation such as, for example, silicone can be swollen in an appropriate chemical agent such as, for example, alcohol, hexane, and/or Freon that also contains the pharmacological agent. By so treating the insulation, the pharmacological agent would diffuse into the insulation only to become trapped therein when the swelling agent is removed by, for example, evaporation, vacuum or other means known in the art. The treated insulation would then be used in the fabrication of the lead 240. Upon implantation of that lead 240, the superficial trapped pharmacological agent would first be released into the tissue, allowing deeper trapped pharmacological agents to migrate to the surface of the polymeric insulation for subsequent release into the tissue.

Figure 8:
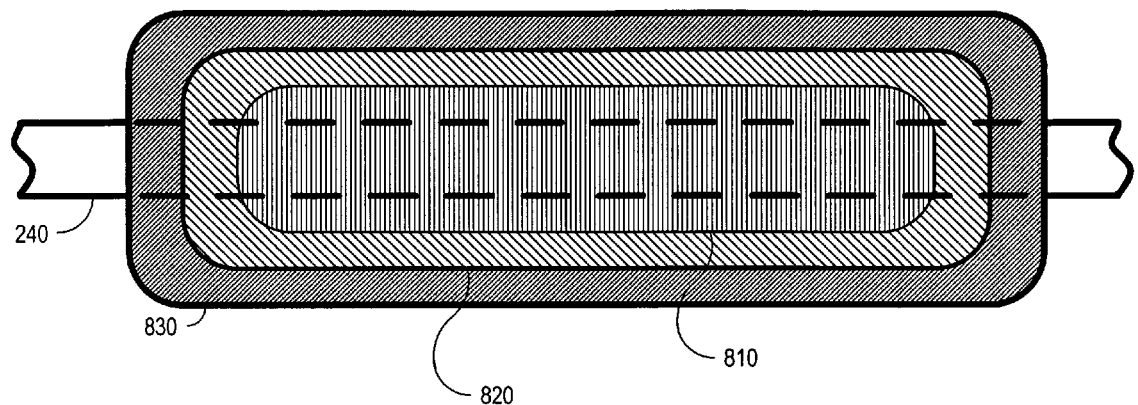
FIG. 8 is a magnified view of another embodiment of a lead with an electrode incorporating pharmacological agents in accordance with the present invention.

Referring now to FIG. 8, a three layer tiered pharmacological delivery approach is illustrated. The lead 240 is illustrated having a first layer 810, a second layer 820, and a third layer 830 on the lead 240. The layers 810, 820, and 830 are configured such that the pharmacological agent in the third layer 830 is delivered first as the third layer 830 is dissolved away and the pharmacological agent diffuses into the tissue and delivers its activity. After the third layer 830 is effectively removed, the second layer 820 is revealed. The pharmacological agent in the second layer 820 is delivered second as the second layer 820 is dissolved away and the pharmacological agent diffuses into the tissue and delivers its activity. After the second layer 820 is effectively removed, the first layer 810 is revealed. The pharmacological agent in the first layer 810 is delivered last as the first layer 810 is dissolved away and the pharmacological agent diffuses into the tissue and delivers its activity.

The layers 810, 820, and 830 may, for example, be continuous or discretely applied at one or a plurality of locations on the length of the lead 240, and have one or more drugs within each of the layers 810, 820 and 830. The layers 810, 820 and 830 may dissolve and/or may remain as a permanent scaffolding after releasing their pharmacological agents.

Figure 9:
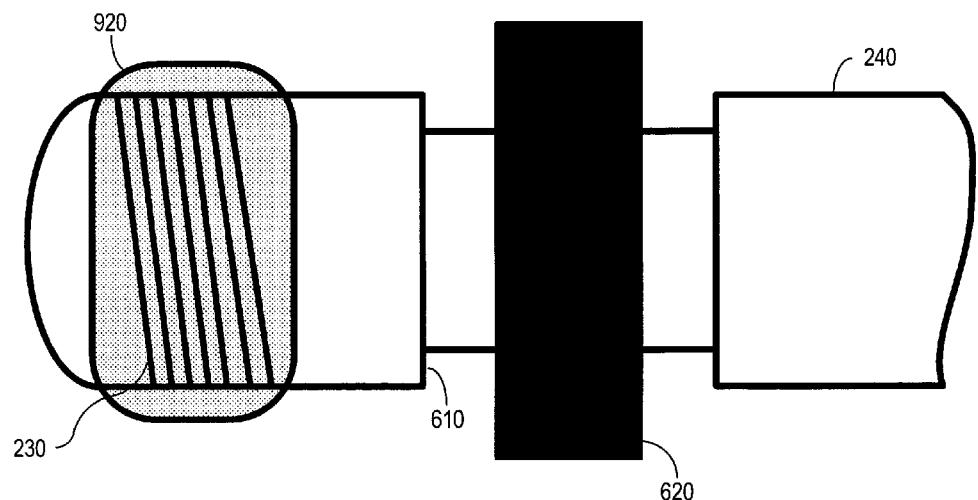
FIG. 9 is a magnified view of another embodiment of a lead with an electrode incorporating pharmacological agents in accordance with the present invention.

FIG. 9 illustrates an embodiment of the present invention that differs from FIG. 6 by the addition of an electrode coating 920 applied over the electrode 230. It may be advantageous to provide a pharmacological delivery to the area of tissue surrounding the electrode 230 of the subcutaneous lead 240. For example, the electrode coating 920 may include an analgesic that is adapted to quickly dissolve off the electrode 230 and diffuse quickly into the surrounding tissue. This would provide an acute reduction in post-operative pain, while not adversely affecting the electrical capabilities of the electrode 230 for use quickly after lead 240 placement into the dissected tissue.

Another application of the electrode coating 920 may be to provide a pharmacological agent that increases the effectiveness of the electrode 230. For example, the electrode coating 920 may include a pharmacological agent that reduces the threshold necessary for pacing, cardioversion, or other activity, such as is disclosed in U.S. Pat. Nos. 4,819,661 and 6,168,801, both of which are hereby incorporated herein by reference.

The electrode coating 920 may be used as the only pharmacological delivery arrangement, and/or may be used in combination with other pharmacological delivery arrangements such as the collar 620 illustrated in FIG. 9 and/or the delivery arrangements illustrated in FIG. 8 and/or other arrangements contemplated herein. As previously discussed, a lead, electrode, and/or can may employ one or more pharmacological agent delivery arrangements on one or more lead, electrode, and/or can component.

Figure 10:
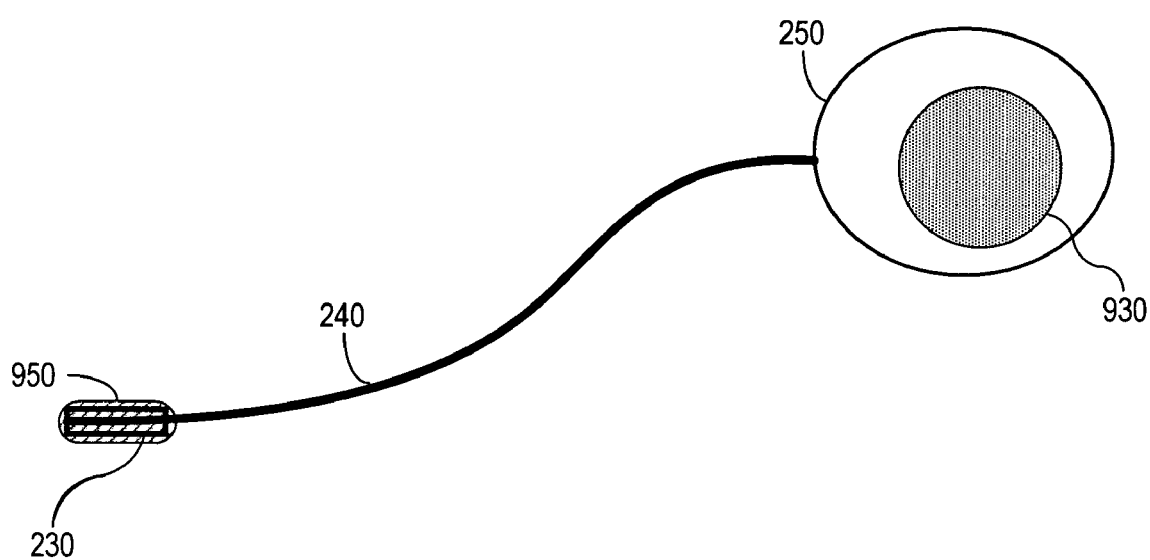
FIG. 10 is a view of another embodiment of a can and lead with an electrode incorporating pharmacological agents in accordance with the present invention.

FIG. 10 illustrates another embodiment of the present invention, with the active can 250 having a pharmacological agent delivery means 930 disposed on the can 250 as well as a tiered pharmacological delivery means 950 disposed on the electrode 230. The lead 240 may also be provided with pharmacological delivery as previously disclosed. The means 930 may partially or completely cover or coat the can 250. Illustrated here in FIG. 10, as described also in earlier embodiments, combinations of pharmacological activity provided with ITCS devices may provide significantly improved outcomes, less morbidity, and improved patient comfort and acceptance.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable lead system, comprising:
a lead comprising a lead body, the lead body comprising a proximal end, a distal end, and a midpoint equidistant from the proximal and distal ends;
a cardiac electrode coupled to the lead body, the electrode and lead body configured for placement within a tunnel surgically formed in subcutaneous non-intrathoracic tissue;
a plurality of fixation elements disposed along the lead body in a spaced relationship between the distal and proximal ends, at least one of the fixation elements situated proximal of the midpoint such that the at least one of the fixation elements is closer to the proximal end than the distal end of the lead body, the at least one of the fixation elements configured to facilitate fixation of a proximal portion of the lead body to a proximal portion of the tunnel, and at least one other of the fixation elements situated distal of the midpoint such that the at least one other of the fixation elements is closer to the distal end than the proximal end of the lead body, the at least one other of the fixation elements configured to facilitate fixation of a distal portion of the lead body to a distal portion of the tunnel; and
a pharmacological agent provided along at least a major portion comprising at least a quarter of the lead body length, the pharmacological agent having a coverage that provides a temporary therapeutic treatment.

2. The lead system according to claim 1, wherein the lead has mechanical memory such that the lead is shape-fitable under manual force to a desired shape and generally retains the shape after implantation.

3. The lead system according to claim 2, wherein the mechanical memory of the lead is facilitated by a braid system incorporated into the lead.

4. The lead system according to claim 1, further comprising an implantable housing containing therapy circuitry coupled to the lead, wherein the lead comprises a rigid elongated structure configured to positionally stabilize the cardiac electrode with respect to the housing such that the rigid elongated structure maintains a particular spacing between the cardiac electrode and the housing.

5. The lead system according to claim 1, further comprising an implantable housing containing therapy circuitry coupled to the lead, wherein the lead and the housing form a rigid unitary structure having an arcuate shape with the cardiac electrode and another electrode near opposing ends of the unitary structure.

6. The lead system according to claim 1, further comprising a sheath located over the lead and covering the pharmacological agent, wherein retraction of the sheath relative to the lead exposes the pharmacological agent and initiates a period of pharmacological activity by the pharmacological agent as the pharmacological agent is allowed to diffuse into tissue.

7. The lead system according to claim 1, further comprising a coating containing the pharmacological agent, the coating applied along the lead and over a removable mask covering the cardiac electrode.

8. The lead system according to claim 1, further comprising:
  a groove in the lead body; and
  a collar seated in the groove, the collar comprising a plurality of layers, each layer having a different one of a plurality of different pharmacological agents, the plurality of different pharmacological agents including the pharmacological agent.

9. The lead system according to claim 1, further comprising:
  a groove in the lead body;
  a collar seated in the groove, the collar containing the pharmacological agent; and
  an encapsulation layer covering the collar, the encapsulation layer comprising a non-dissolving semi-permeable membrane that regulates diffusion of the pharmacological agent.

10. The system of claim 1, wherein the plurality of fixation elements are tissue penetrating elements.

11. The system of claim 1, wherein the plurality of fixation elements are tines.

12. The system of claim 1, wherein at least one of the plurality of fixation elements comprises an expandable fixation element.

13. The system of claim 1, wherein the at least one other of the fixation elements situated distal of the midpoint is a tissue penetrating helix and the at least one of the fixation elements situated proximal to the midpoint is an expandable fixation element.

14. An implantable system, comprising:
  a can;
  a lead comprising a lead body, the lead body extending from the can and comprising a proximal end, and distal end, and a midpoint between the proximal and distal ends;
  a cardiac electrode coupled to the lead body, the electrode and the lead body configured for placement within a tunnel surgically formed in subcutaneous non-intrathoracic tissue;
  a plurality of fixation elements disposed along the lead body in a spaced relationship between the distal and proximal ends, at least one of the fixation elements situated proximal of the midpoint such that the at least one of the fixation elements is closer to the proximal end than the distal end of the lead body, the at least one of the fixation elements configured to facilitate fixation of a proximal portion of the lead body to a proximal portion of the tunnel, and at least one other of the fixation elements situated distal of the midpoint such that the at least one other of the fixation elements is closer to the distal end than the proximal end of the lead body, the at least one other of the fixation elements configured to facilitate fixation of a distal portion of the lead body to a distal portion of the tunnel; and
  a pharmacological agent provided along at least a major portion comprising at least a quarter of the lead body length, the pharmacological agent having a coverage that provides a temporary therapeutic treatment.

15. The implantable system according to claim 14, wherein the temporary therapeutic treatment is localized to an area substantially surrounding a subcutaneous dissection path.

16. The implantable system according to claim 14, wherein a duration of the pharmacological agent's effectiveness is shorter than about 1 hour.

17. The implantable system according to claim 14, wherein a duration of the pharmacological agent's effectiveness is shorter than about 2 days.

18. The implantable system according to claim 14, wherein the pharmacological agent comprises an analgesic or an anesthetic.

19. The implantable system according to claim 14, wherein the pharmacological agent comprises an antibiotic or an antiseptic.

20. The implantable system according to claim 14, wherein the pharmacological agent comprises a steroid or an anti-inflammatory agent.

21. The implantable system according to claim 14, wherein the pharmacological agent comprises an agent that promotes hemostasis or provides vasoconstriction.

22. The implantable system according to claim 14, wherein the pharmacological agent comprises collagen or an agent that increases a rate of healing.

23. An implantable lead, comprising:
  a lead body comprising a proximal end, a distal end, and a midpoint between the proximal and distal ends;
  a cardiac electrode coupled to the lead body, the electrode and lead body configured for placement within a tunnel surgically formed in subcutaneous non-intrathoracic tissue;
  a plurality of fixation elements disposed along the lead body in a spaced relationship between the distal and proximal ends, at least one of the fixation elements situated proximal to the midpoint such that the at least one of the fixation elements is closer to the proximal end than the distal end of the lead body, the at least one of the fixation elements configured to facilitate fixation of a proximal portion of the lead body to a proximal portion of the tunnel, and at least one other of the fixation elements situated distal of the midpoint such that the at least one other of the fixation elements is closer to the distal end than the proximal end of the lead body, the at least one other of the fixation elements configured to facilitate fixation of a distal portion of the lead body to a distal portion of the tunnel; and
  a pharmacological agent provided on at least a major portion of the lead body, including the electrically active portions of the electrode, the pharmacological agent having a coverage that provides a temporary therapeutic treatment, the electrically active portions of the electrode remaining electrically active for delivering cardiac stimulation energy through the pharmacological agent at the electrically active portions after provision of the pharmacological agent.

24. The lead according to claim 23, wherein the temporary therapeutic treatment is localized to an area substantially surrounding a subcutaneous dissection path.

25. The lead according to claim 23, wherein a duration of the pharmacological agent's effectiveness is shorter than about 1 hour.

26. The lead according to claim 23, wherein the electrode further comprises a collar, the pharmacological agent disposed at the collar.

27. The lead according to claim 23, wherein the lead further comprises a polymeric structure, the pharmacological agent infused within the polymeric structure.

28. The lead according to claim 23, wherein the electrode further comprises a porous region, the pharmacological agent at least partially filling pores of the porous region.

29. The lead according to claim 23, wherein at least a portion of the electrode comprises a coating, the coating comprising the pharmacological agent.

30. The lead according to claim 29, wherein the coating covers at least 25% of a surface area of the electrode.

31. The lead according to claim 23, wherein the pharmacological agent comprises an analgesic or an anesthetic.

32. The lead according to claim 23, wherein the pharmacological agent comprises an antibiotic or an antiseptic.

33. The lead according to claim 23, wherein the pharmacological agent comprises a steroid or an anti-inflammatory agent.

34. The lead according to claim 23, wherein the pharmacological agent comprises an agent that promotes hemostasis or provides vasoconstriction.

35. The lead according to claim 23, wherein the pharmacological agent comprises collagen or an agent that increases a rate of healing.

36. An implantable lead, comprising:
a lead body comprising a proximal end, a distal end, and a midpoint between the proximal and distal ends;
a cardiac electrode assembly coupled to the lead body, the electrode assembly and the lead body configured for placement within a tunnel surgically formed in subcutaneous non-intrathoracic tissue;
a plurality of fixation elements disposed along the lead body in a spaced relationship between the distal and proximal ends, at least one of the fixation elements situated proximal to the midpoint such that the at least one of the fixation elements is closer to the proximal end than the distal end of the lead body, the at least one of the fixation elements configured to facilitate fixation of a proximal portion of the lead body to a proximal portion of the tunnel, and at least one other of the fixation elements situated distal of the midpoint such that the at least one other of the fixation elements is closer to the distal end than the proximal end of the lead body, the at least one other of the fixation elements configured to facilitate fixation of a distal portion of the lead body to a distal portion of the tunnel; and
a plurality of pharmacological agents provided along at least a major portion of the lead, the pharmacological agents providing a plurality of temporary therapeutic treatments to the subcutaneous non-intrathoracic tissue, at least one of the pharmacological agents providing a temporary therapeutic treatment.

37. The lead according to claim 36, wherein the lead body has mechanical memory such that the lead body is shape-fitable under manual force to a desired shape and generally retains the shape after implantation.

38. The lead according to claim 37, wherein the mechanical memory of the lead body is facilitated by a braid system incorporated into the lead body.

39. The lead according to claim 36, further comprising an implantable housing containing therapy circuitry coupled to the lead body, wherein the lead body comprises a rigid elongated structure configured to positionally stabilize the cardiac electrode with respect to the housing such that the rigid elongated structure maintains a particular spacing between the cardiac electrode and the housing.

40. The lead according to claim 36, further comprising an implantable housing containing therapy circuitry coupled to the lead body, wherein the lead body and the housing form a rigid unitary structure having an arcuate shape with the cardiac electrode and another electrode on opposing ends of the unitary structure.

41. The lead according to claim 36, further comprising a sheath located over the lead body and covering the pharmacological agent, wherein retraction of the sheath relative to the lead body exposes the pharmacological agent and initiates a period of pharmacological activity by the pharmacological agent as the pharmacological agent is allowed to diffuse into tissue.

42. The lead according to claim 36, further comprising a coating containing at least one pharmacological agent of the plurality, the coating applied along the lead body and over a removable mask covering the cardiac electrode.

43. The lead according to claim 36, further comprising:
a groove in the lead body; and
a collar seated in the groove, the collar comprising a plurality of layers, each layer containing a different one of the plurality of pharmacological agents.

44. The lead according to claim 36, wherein the electrode assembly comprises a porous region, a first pharmacological agent of the plurality of pharmacological agents at least partially filling pores of the porous region.

45. The lead according to claim 44, wherein at least a portion of the electrode assembly comprises a coating, the coating comprising a second pharmacological agent of the plurality of pharmacological agents.

46. The lead according to claim 44, wherein at least a portion of the electrode assembly comprises a second pharmacological agent of the plurality of pharmacological agents, the second pharmacological agent covering at least a portion of the first pharmacological agent, thereby delaying release of at least a portion of the first pharmacological agent until after at least a majority of an effective period of the second pharmacological agent has elapsed.

47. The lead according to claim 46, wherein the second pharmacological agent comprises an analgesic or an anesthetic, and the first pharmacological agent comprises an antibiotic or an antiseptic.

48. The lead according to claim 46, wherein a duration of the second pharmacological agent's effectiveness is shorter than about 1 hour and a duration of the first pharmacological agent's effectiveness is longer than about 1 day.

49. The lead according to claim 46, wherein the second pharmacological agent comprises an analgesic and an antiseptic, and the first pharmacological agent comprises an antibiotic.

50. The lead according to claim 36, wherein at least a first pharmacological agent of the plurality of pharmacological agents is disposed as a coating on at least a portion of the electrode assembly.

51. The lead according to claim 50, wherein the coating covers at least 25% of a surface area of the electrode assembly.

52. The lead according to claim 50, wherein a second pharmacological agent of the plurality of pharmacological agents is disposed as a coating on at least a portion of the first pharmacological coating.

53. The lead according to claim 52, wherein the second pharmacological agent comprises an analgesic or an anesthetic, and the first pharmacological agent comprises an antibiotic or an antiseptic.

54. The lead according to claim 36, further comprising:
a groove in the lead body;
a collar seated in the groove, the collar containing at least one of the plurality of pharmacological agents; and
an encapsulation layer covering the collar, the encapsulation layer comprising a non-dissolving semi-permeable membrane that regulates diffusion of the at least one pharmacological agent from the collar.

55. The lead according to claim 36, wherein at least one of the pharmacological agents of the plurality of pharmacological agents comprises an analgesic or an anesthetic.

56. The lead according to claim 36, wherein at least one of the pharmacological agents of the plurality of pharmacological agents comprises an antibiotic or an antiseptic.

57. The lead according to claim 36, wherein at least one of the pharmacological agents of the plurality of pharmacological agents comprises a steroid or an anti-inflammatory agent.

58. The lead according to claim 36, wherein at least one of the pharmacological agents of the plurality of pharmacological agents comprises an agent that promotes hemostasis or provides vasoconstriction.

59. A method of lead implantation, comprising:
delivering into subcutaneous non-intrathoracic chest tissue along the rib cage, a cardiac lead comprising a lead body, a proximal end, a distal end, a midpoint between the proximal and distal ends, a proximal portion, a distal portion, a cardiac electrode, a plurality of fixation elements disposed along the lead body in a spaced relationship between the distal and proximal ends, at least one of the fixation elements situated proximal to the midpoint such that the at least one of the fixation elements is closer to the proximal end than the distal end of the lead and at least one other of the fixation elements situated distal of the midpoint such that the at least one other of the fixation elements is closer to the distal end than the proximal end of the lead, the cardiac lead having a pharmacological agent along at least a major portion of the lead body;
fixing the proximal portion of the lead body to a proximal portion of the tunnel using the at least one of the fixation elements situated proximal to the midpoint and fixing the distal portion of the lead body to a distal portion of the tunnel using the at least one other of the fixation elements situated distal of the midpoint; and
delivering the pharmacological agent from the lead body to subcutaneous non-intrathoracic chest tissue substantially surrounding the lead body, the pharmacological agent providing a temporary therapeutic treatment.

60. The method according to claim 59, wherein the plurality of fixation elements, including the at least one of the fixation elements and the at least one other of the fixation elements, comprise a plurality of tines.

61. The method according to claim 59, wherein delivering the pharmacological agent comprises delivering a first agent having a first activity and delivering a second agent having a second activity.

62. The method according to claim 61, wherein the first activity occurs for shorter than about 1 hour and the second activity occurs for longer than about 1 hour.

63. The method according to claim 61, wherein the first activity comprises analgesia or anesthesia and the second activity comprises antisepsis or antibiosis.

64. The method according to claim 61, wherein the first activity lasts shorter than about 1 hour and the second activity lasts more than about 1 day.

65. An implantable lead, comprising:
a lead body comprising a proximal end, a distal end, and a midpoint equidistant from the proximal and distal ends;
a cardiac electrode coupled to the lead body, the electrode configured for subcutaneous non-intrathoracic placement in a patient;
a plurality of fixation elements disposed along the lead body in a spaced relationship between the distal and proximal ends, at least one of the fixation elements situated proximal to the midpoint such that the at least one of the fixation elements is closer to the proximal end than the distal end of the lead body and at least one other of the fixation elements situated distal of the midpoint such that the at least one other of the fixation elements is closer to the distal end than the proximal end of the lead body; and
means for delivering a pharmacological agent from at least a major portion of the lead body to subcutaneous non-intrathoracic tissue substantially surrounding the lead body.

66. The lead according to claim 65, wherein the lead body has mechanical memory such that the lead body is shape-fitable under manual force to a desired shape and generally retains the shape after implantation.

67. The lead according to claim 65, further comprising an implantable housing containing therapy circuitry coupled to the lead body, wherein the lead body comprises a rigid elongated structure configured to positionally stabilize the cardiac electrode with respect to the housing such that the rigid elongated structure maintains a particular spacing between the cardiac electrode and the housing.

68. The lead according to claim 65, further comprising an implantable housing containing therapy circuitry coupled to the lead body, wherein the lead body and the housing form a rigid unitary structure having an arcuate shape with the cardiac electrode and another electrode near opposing ends of the unitary structure.

69. The lead according to claim 65, further comprising a sheath located over the lead body and covering the pharmacological agent, wherein retraction of the sheath relative to the lead body exposes the pharmacological agent and initiates a period of pharmacological activity by the pharmacological agent as the pharmacological agent is allowed to diffuse into tissue.

70. The lead according to claim 65, further comprising a coating containing the pharmacological agent, the coating applied along the lead body and over a removable mask covering the cardiac electrode.

71. The lead according to claim 65, further comprising:
a groove in the lead body;
a collar seated in the groove, the collar containing the pharmacological agent; and
an encapsulation layer covering the collar, the encapsulation layer comprising a non-dissolving semi-permeable membrane that regulates diffusion of the pharmacological agent.

72. An implantable system, comprising:
a can;
a lead comprising a lead body, a proximal end, a proximal portion, a distal end a midpoint equidistant from the proximal end and the distal end, and a distal portion, provided with the can;
a cardiac electrode coupled to the lead body, the electrode and lead body configured for subcutaneous non-intrathoracic placement within a tunnel surgically formed within subcutaneous non-intrathoracic tissue of a patient;
a plurality of fixation elements disposed along the lead body in a spaced relationship between the distal and proximal ends, at least one of the fixation elements situated proximal to the midpoint such that the at least one of the fixation elements is closer to the proximal end than the distal end of the lead body, the at least one of the fixation elements configured to facilitate fixation of the proximal portion of the lead body to a proximal portion of the tunnel, and at least one other of the fixation elements situated distal of the midpoint such that the at least one other of the fixation elements is closer to the distal end than the proximal end of the lead body, the at least one other of the fixation elements configured to facilitate fixation of the distal portion of the lead body to a distal portion of the tunnel; and
a pharmacological agent provided on the can, a major portion of the lead body, and the electrically active portions of the electrode, the pharmacological agent providing a temporary therapeutic treatment to subcutaneous non-intrathoracic tissue adjacent the can, lead body, and electrode, respectively, the electrically active portions of at least the electrode remaining electrically active for delivering cardiac stimulation energy through the pharmacological agent after provision of the pharmacological agent.

73. The system according to claim 72, wherein the lead comprises a rigid elongated structure configured to positionally stabilize the cardiac electrode with respect to the can such that the rigid elongated structure maintains a particular spacing between the cardiac electrode and the can.

74. The system according to claim 72, further comprising a sheath located over the lead and covering the pharmacological agent on the lead, wherein retraction of the sheath relative to the lead exposes the pharmacological agent on the lead and initiates a period of pharmacological activity by the pharmacological agent as the pharmacological agent is allowed to diffuse into tissue.

75. The system according to claim 72, wherein the lead and the can form a rigid unitary structure having an arcuate shape with the cardiac electrode and another electrode near opposing ends of the rigid unitary structure.

76. The system according to claim 72, wherein the lead has mechanical memory such that the lead is shape-fitable under manual force to a desired shape and retains the shape after implantation.

77. The system according to claim 76, wherein the mechanical memory of the lead is facilitated by a braid system incorporated into the lead.

78. The system according to claim 72, further comprising a coating containing the pharmacological agent, the coating applied along the lead and over a removable mask covering the cardiac electrode.

79. The system according to claim 72, further comprising:
a groove in the lead body; and
a collar seated in the groove, the collar comprising a plurality of layers, each layer having a different one of a plurality of different pharmacological agents, the plurality of different pharmacological agents including the pharmacological agent.

80. The system according to claim 72, further comprising:
a groove in the lead body;
a collar seated in the groove, the collar containing the pharmacological agent; and
an encapsulation layer covering the collar, the encapsulation layer comprising a non-dissolving semi-permeable membrane that regulates diffusion of the pharmacological agent from the collar.

81. The system according to claim 72, wherein the plurality of fixation elements comprises a plurality of tines.

82. The system according to claim 72, wherein the pharmacological agent comprises collagen or an agent that increases a rate of healing.

83. An implantable lead configured for placement within a tunnel surgically formed in subcutaneous non-intrathoracic tissue, comprising:
a lead body comprising a proximal end, a distal end, and a midpoint between the proximal and distal ends;
a plurality of pharmacological agents provided on a major portion of the lead body, the pharmacological agents providing a plurality of temporary therapeutic treatments to the subcutaneous non-intrathoracic tissue;
a plurality of fixation elements disposed along the lead body in a spaced relationship between the distal and proximal ends, at least one of the fixation elements situated proximal to the midpoint such that the at least one of the fixation elements is closer to the proximal end than the distal end of the lead body, the at least one of the fixation elements configured to facilitate fixation of a proximal portion of the lead body to a proximal portion of the tunnel, and at least one other of the fixation elements situated distal of the midpoint such that the at least one other of the fixation elements is closer to the distal end than the proximal end of the lead body, the at least one other of the fixation elements configured to facilitate fixation of a distal portion of the lead body to a distal portion of the tunnel; and
an electrode coupled to the lead body, the electrode configured for subcutaneous non-intrathoracic placement within a patient, wherein a first pharmacological agent is provided on at least electrically active portions of the electrode, and the electrically active portions of the electrode remain electrically active for delivering cardiac stimulation energy through the first pharmacological agent after provision of the first pharmacological agent.

84. The lead according to claim 83, wherein at least one of the plurality of pharmacological agents is provided at a plurality of locations on the lead body.

85. The lead according to claim 83, wherein at least two of the plurality of pharmacological agents are provided at a plurality of locations on the lead body.

86. The lead according to claim 83, wherein a duration of effectiveness of at least one of the plurality of pharmacological agents or the first pharmacological agent is shorter than about 1 hour.

87. The lead according to claim 83, wherein a duration of effectiveness of at least two of the plurality of pharmacological agents or the first pharmacological agent is shorter than about 1 hour.

88. The lead according to claim 83, wherein the lead comprises a collar, at least one of the pharmacological agents disposed at the collar.

89. The lead according to claim 83, wherein the lead further comprises a polymeric structure, at least one of the plurality of pharmacological agents infused within the polymeric structure.

90. The lead according to claim 83, wherein a second pharmacological agent of the plurality of pharmacological agents is disposed as a coating on at least a portion of the lead.

91. The lead according to claim 90, wherein the second pharmacological agent covers at least a portion of a porous region of the lead body, thereby delaying release of at least a portion of one of the plurality of pharmacological agents until after commencement of an effective period of the second pharmacological agent.

92. The lead according to claim 91, wherein the second pharmacological agent comprises an analgesic or an anesthetic, and the first pharmacological agent comprises an antibiotic or an antiseptic.

93. The lead according to claim 90, wherein a duration of the second pharmacological agent's effectiveness is shorter than about 1 hour and a duration of the first pharmacological agent's effectiveness is longer than about 1 day.

94. The lead according to claim 90, wherein the second pharmacological agent comprises an analgesic and an antiseptic, and the first pharmacological agent comprises an antibiotic.

95. The lead according to claim 83, wherein at least one of the plurality of pharmacological agents or the first pharmacological agent comprises an analgesic or an anesthetic.

96. The lead according to claim 83, wherein at least one of the plurality of pharmacological agents or the first pharmacological agent comprises an antibiotic or an antiseptic.

97. The lead according to claim 83, wherein at least one of the plurality of pharmacological agents or the first pharmacological agent comprises a steroid or an anti-inflammatory agent.

98. The lead according to claim 83, wherein at least one of the plurality of pharmacological agents or the first pharmacological agent comprises an agent that promotes hemostasis or provides vasoconstriction.

99. An implantable system, comprising:
a can;
a lead provided with the can, the lead including a lead body, a proximal end, a proximal portion, a distal end, a distal portion, a midpoint equidistant from the distal and proximal ends, and an electrode, coupled to the lead body, the lead body and electrode configured for placement within a tunnel surgically formed in subcutaneous non-intrathoracic tissue;
a plurality of fixation tines disposed along the lead body in a spaced relationship between the distal and proximal ends, at least one of the fixation tines situated proximal to the midpoint such that the at least one of the fixation tines is closer to the proximal end than the distal end of the lead body, the at least one of the fixation tines configured to facilitate fixation of the proximal portion of the lead body to a proximal portion of the tunnel, and at least one other of the fixation tines situated distal of the midpoint such that the at least one other of the fixation tines is closer to the distal end than the proximal end of the lead body, the at least one other of the fixation tines configured to facilitate fixation of the distal portion of the lead body to a distal portion of the tunnel;
a first pharmacological agent provided on at least the proximal portion of the lead, the first pharmacological agent providing a temporary therapeutic treatment; and
a second pharmacological agent provided on the can, the second pharmacological agent providing a temporary therapeutic treatment to subcutaneous non-intrathoracic tissue.

100. The system according to claim 99, wherein the lead has mechanical memory such that the lead is shape-fitable under manual force to a desired shape and generally retains the shape after implantation.

101. The system according to claim 100, wherein the mechanical memory of the lead is facilitated by a braid system incorporated into the lead.

102. The system according to claim 99, wherein the lead comprises a rigid elongated structure configured to positionally stabilize the cardiac electrode with respect to the can such that the rigid elongated structure maintains a particular spacing between the cardiac electrode and the can.

103. The system according to claim 99, wherein the lead and the can form a rigid unitary structure having an arcuate shape with the cardiac electrode and at least one other electrode near opposing ends of the unitary structure.

104. The system according to claim 103, further comprising a sheath located over the lead and covering the first pharmacological agent, wherein retraction of the sheath relative to the lead exposes the first pharmacological agent and initiates a period of pharmacological activity by the first pharmacological agent as the first pharmacological agent is allowed to diffuse into tissue.

105. The system according to claim 99, further comprising a coating containing the first pharmacological agent, the coating applied along the lead and over a removable mask covering the cardiac electrode.

106. The system according to claim 99, further comprising:
a groove in the lead body;
a collar seated in the groove, the collar containing the first pharmacological agent; and
an encapsulation layer covering the collar, the encapsulation layer comprising a non-dissolving semi-permeable membrane that regulates diffusion of the pharmacological agent.

107. The system according to claim 99, wherein one or both of the first and second pharmacological agents comprises a steroid or an anti-inflammatory agent.

108. The system according to claim 99, wherein one or both of the first and second pharmacological agents comprises an agent that promotes hemostasis or provides vasoconstriction.

109. The system according to claim 99, wherein one or both of the first and second pharmacological agents comprises collagen or an agent that increases a rate of healing.

110. The system according to claim 99, wherein a duration of effectiveness of the first pharmacological agent is about equal to a duration of effectiveness of the second pharmacological agent.

111. The system according to claim 99, wherein a duration of effectiveness of the first pharmacological agent is longer than about 1 day and a duration of effectiveness of the second pharmacological agent is shorter than about 2 hours.

* * * * *